(12) United States Patent
Oestreich

(10) Patent No.: US 6,257,895 B1
(45) Date of Patent: Jul. 10, 2001

(54) JAW MODEL

(76) Inventor: Gerd Oestreich, URB El Maquilishuat, Calle Jacaranda Pasaje PG J4 No. 2, El Salvador (SV)

( * ) Notice: Subject to any disclaimer, the term of this patent is extended or adjusted under 35 U.S.C. 154(b) by 0 days.

(21) Appl. No.: 09/545,307

(22) Filed: Apr. 6, 2000

(30) Foreign Application Priority Data

Apr. 12, 1999 (DE) .............................................. 199 17 759

(51) Int. Cl.$^7$ .................................................. A61K 11/00
(52) U.S. Cl. ........................................... 434/274; 434/263
(58) Field of Search .................................. 434/274, 263, 434/264; 433/74, 213

(56) References Cited

U.S. PATENT DOCUMENTS

| 1,948,059 | * | 2/1934 | Baugh | 434/263 |
|---|---|---|---|---|
| 2,812,578 | * | 11/1957 | Weidenhamer | 434/263 |
| 3,286,350 | * | 11/1966 | Cooper | 433/213 |
| 3,458,936 | * | 8/1969 | Schulz | 434/263 |
| 3,787,979 | * | 1/1974 | Acevedo | 434/263 |
| 3,908,272 | * | 9/1975 | Arnold | 434/263 |
| 4,840,565 | | 6/1989 | Poveromo . | |
| 4,846,684 | * | 7/1989 | Oesterich | 433/213 |
| 4,902,232 | * | 2/1990 | Neustadter | 434/263 |
| 4,969,820 | * | 11/1990 | Oesterich | 434/264 |
| 5,030,102 | * | 7/1991 | Lang | 434/263 |

FOREIGN PATENT DOCUMENTS 10-8403978   10/1984   (WO) .

* cited by examiner

Primary Examiner—Jacob K. Ackun, Jr.
Assistant Examiner—K Fernstrom
(74) Attorney, Agent, or Firm—Mark P. Stone

(57) ABSTRACT

In a jaw model for demonstrating dental work, anchoring parts (2) designed as imitation tooth stumps and guided in bore holes (10) of a main body (1) are used for securing the workpieces which consist in particular of individual teeth or bridges. To be able to quickly adapt the position and number of the post-shaped anchoring parts (2) to different demonstration conditions, the anchoring parts (2) are spring-mounted in the bore holes (10) so that they can be easily transferred from a first locked position, in which their end is flush with the surface of the main body (1), into a second locked position in which they can be used for securing the respective workpiece.

18 Claims, 10 Drawing Sheets

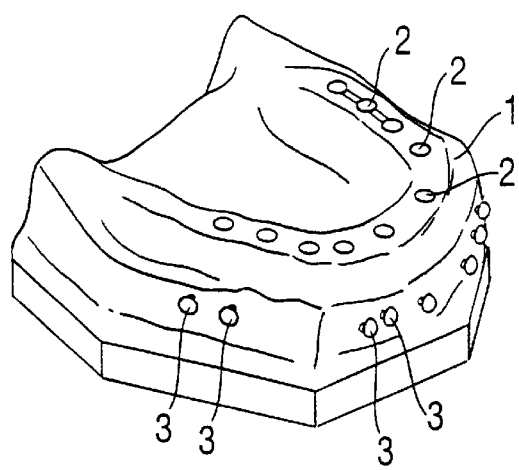 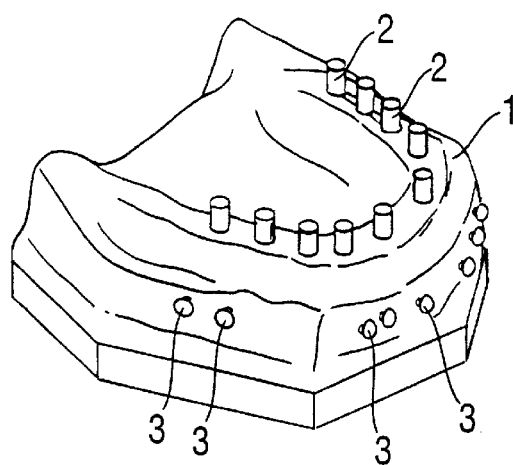
Fig. 1    Fig. 2
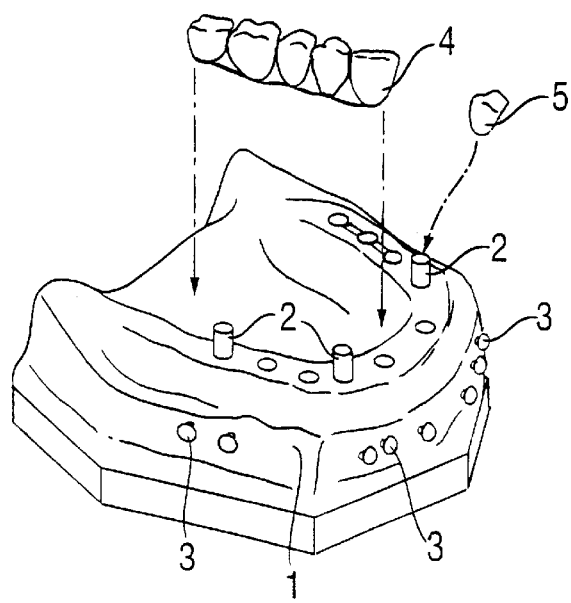 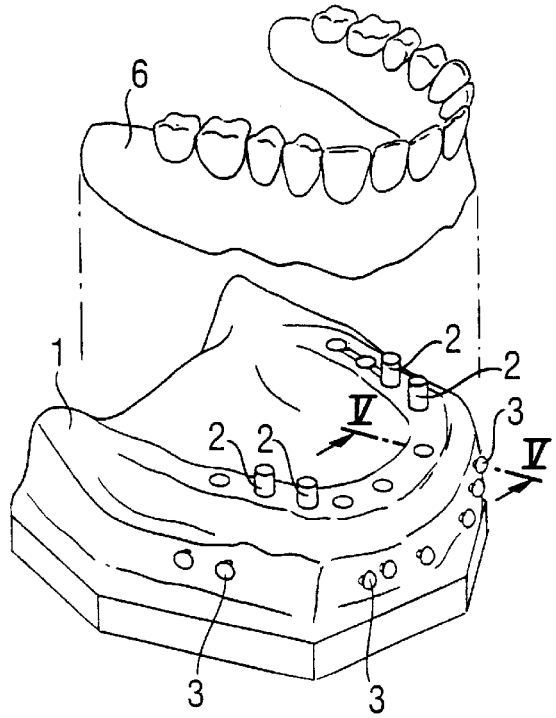
Fig. 3    Fig. 4

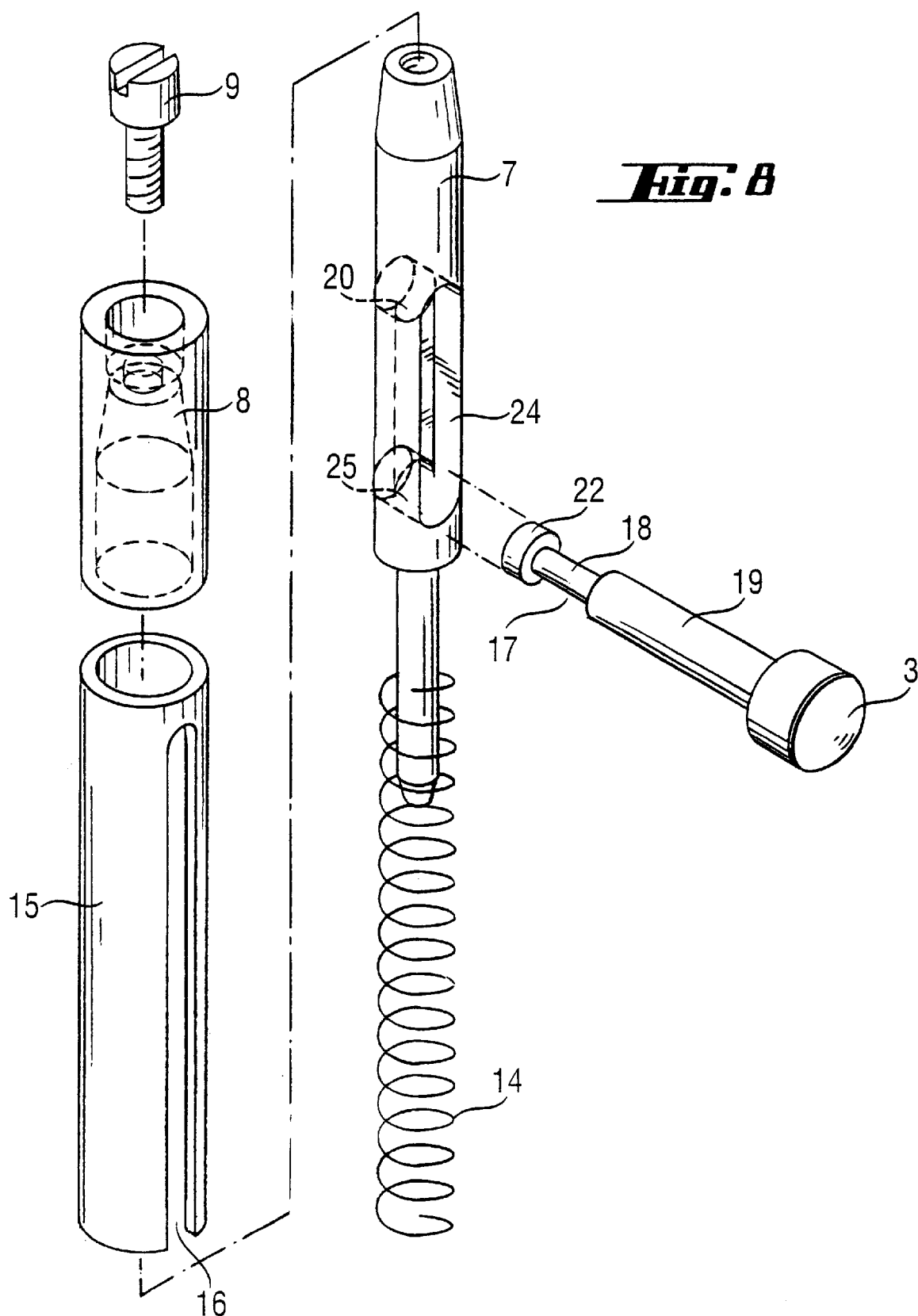

JAW MODEL

BACKGROUND OF THE INVENTION

The invention relates to a jaw model for demonstrating dental work, with a main body which is designed in the manner of a jaw arch and has a multiplicity of bore holes for receiving post-shaped anchoring parts which can be used as imitation tooth stumps.

A jaw model of the above type is known from WO 84/03978. In the known model, depending on the type of prosthetic dental work, posts already connected to the workpieces or intended to be connected to them can be inserted, from that side of the main body directed towards the oral cavity, into bore holes provided in this main body. In order to be able easily to remove the posts or the individual teeth, bridges, etc. connected to them, the bore holes are continuous holes and the posts are made so long that they project beyond the edge of the respective bore hole on that side of the main body directed away from the oral cavity. Consequently, it is possible, if so required, to exert pressure on those ends of the posts protruding beyond the edge of the bore hole.

From U.S. Pat. No. 4,840,565 it is also known, in the case of a jaw model, for posts already connected to prosthetic workpieces to be locked in the bore holes provided for them. For this purpose, the posts are provided with transverse bore holes for receiving locking pins which hold the prosthetic workpiece in its intended position relative to the jaw arch. In this case too, the bore holes are continuous and the posts are sufficiently long for them to be removed again in the same way as the posts in the known jaw model described above.

SUMMARY OF THE INVENTION

The known models are not entirely satisfactory. Thus, in both solutions, not only is the application and removal of the posts comparatively awkward and time-consuming, there is also the risk that posts or the prosthetic workpieces securely connected to them and consisting of individual teeth will be lost. The invention is based on the object of making available a jaw model of the generic type in question which permits convenient, quick and clear presentation of different possible solutions for securing dental prosthetic workpieces on an upper or lower jaw. According to the invention, this object is achieved by the fact that anchoring parts are guided non-removably in the bore holes and, by means of a spring acting on them, can be transferred from a first locked position into a second locked position and, when the force of the spring is overcome, can be transferred from the second locked position back into the first locked position, their end in the first locked position being flush with the surface of the main body, while in the second locked position it projects above the surface of the main body.

The jaw model according to the invention is extraordinarily easy to use and is suitable not only for providing explanations to patients, but also for training students and dental technicians. Because of its convenience, it permits alternatives to be sought for attaining an optimum solution.

BRIEF DESCRIPTION OF THE DRAWINGS

Further details and features of the invention are evident from the dependent claims and from the following description of two embodiments of the invention illustrated in the attached drawing, in which:

FIG. 2 shows the jaw model according to FIG. 1, in which all the anchoring parts are "driven out", FIG. 3 shows the jaw model according to FIG. 1, with three anchoring parts driven out for securing an individual tooth and a bridge, FIG. 4 shows the jaw model according to FIG. 1, with four anchoring parts driven out for securing a total prosthesis, FIG. 7 shows a section corresponding to FIG. 5, with the anchoring part driven out, FIG. 8 shows individual parts of FIGS. 5 to 7 in a perspective and exploded view.

DESCRIPTION OF THE BEST MODES FOR CARRYING OUT THE INVENTION

Figure 5:
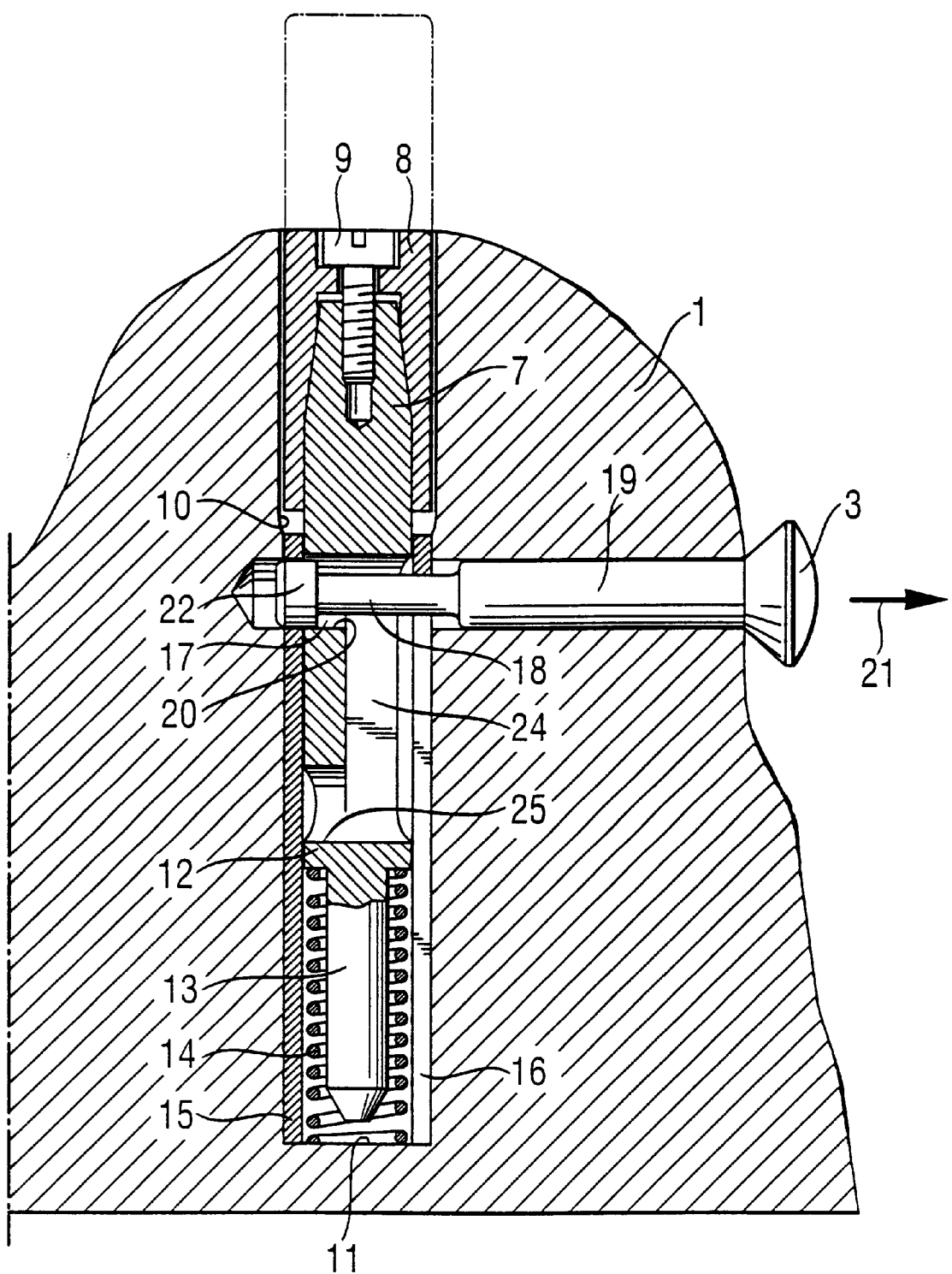
FIG. 5 shows, on an enlarged scale, a section along the line V—V in FIG. 4.
Figure 6:
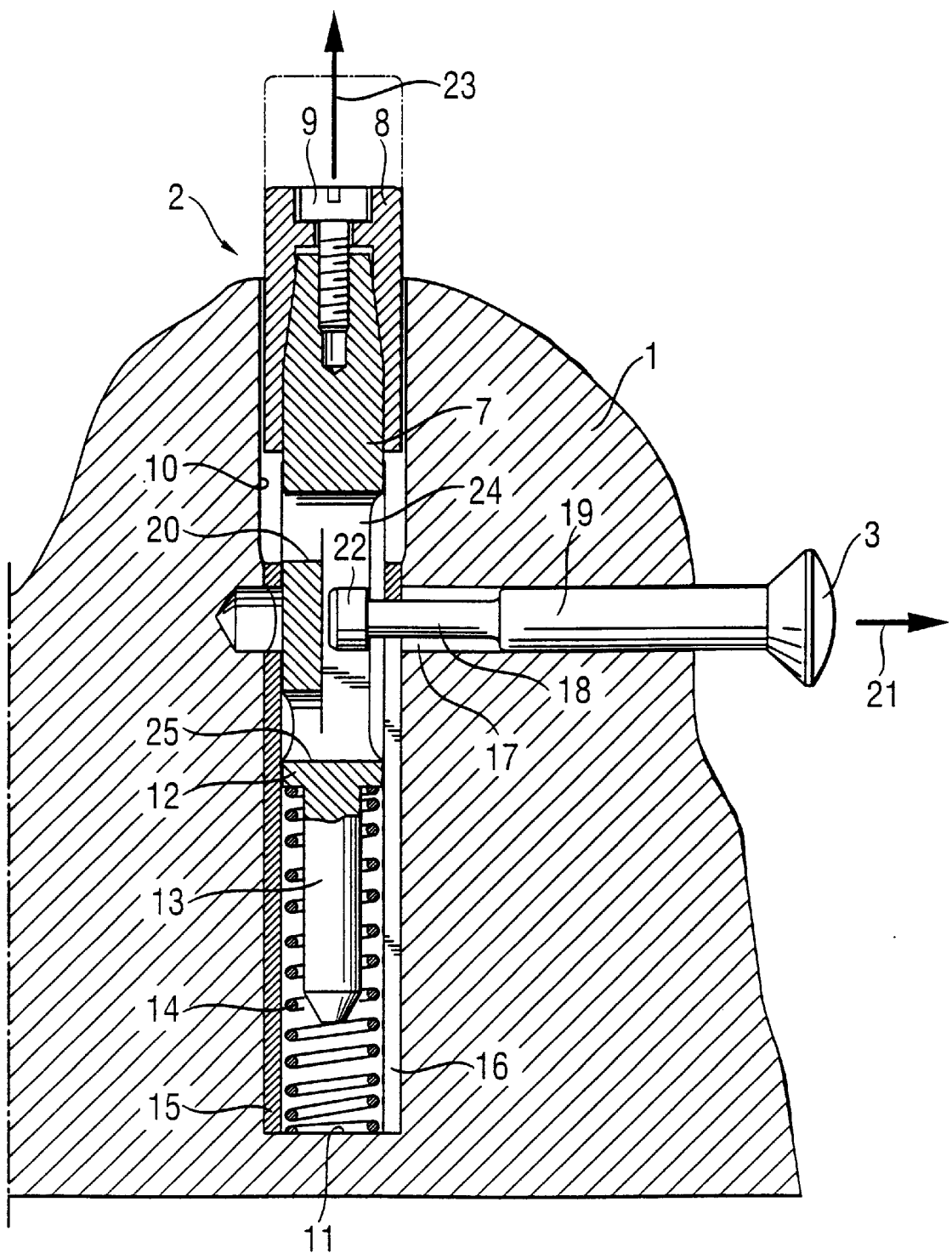
FIG. 6 shows a section, corresponding to FIG. 5, with the anchoring part in an intermediate position as it is being driven out.
Figure 1:
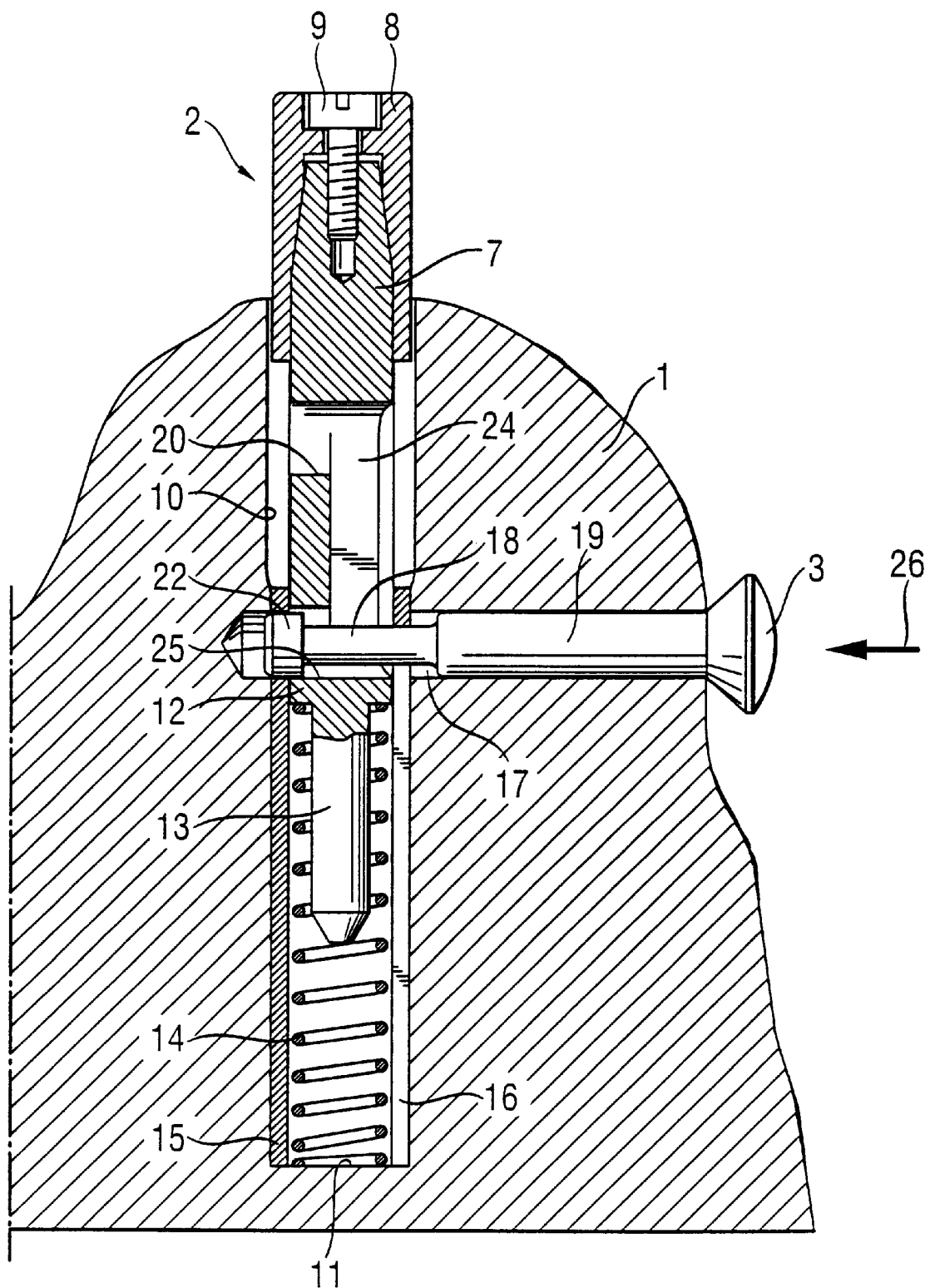
FIG. 1 shows a jaw model in which all the anchoring parts are "driven home"
Figure 9:
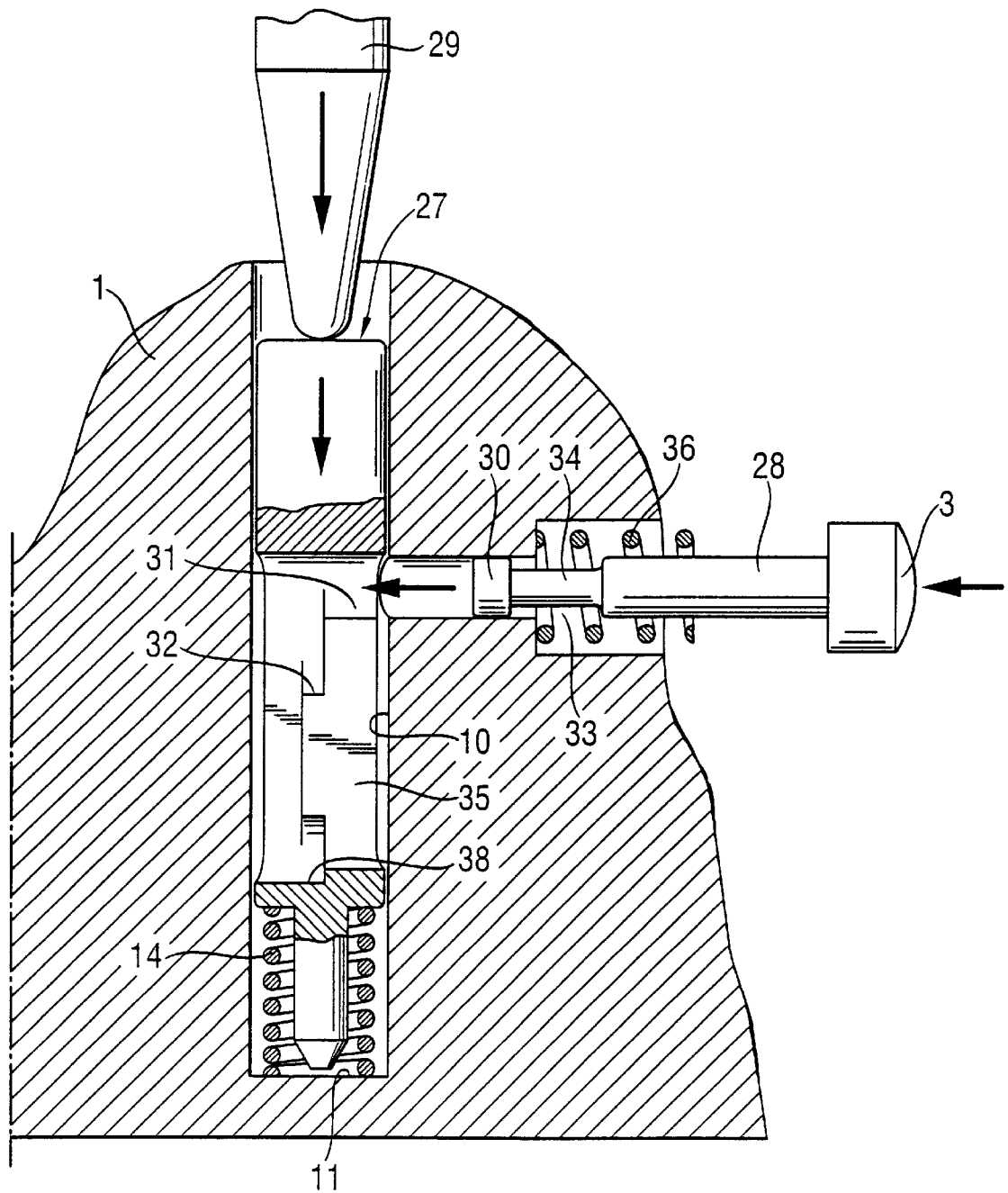
FIG. 9 shows a section corresponding to FIG. 5, through a second embodiment during fitting of the anchoring part.
Figure 10:
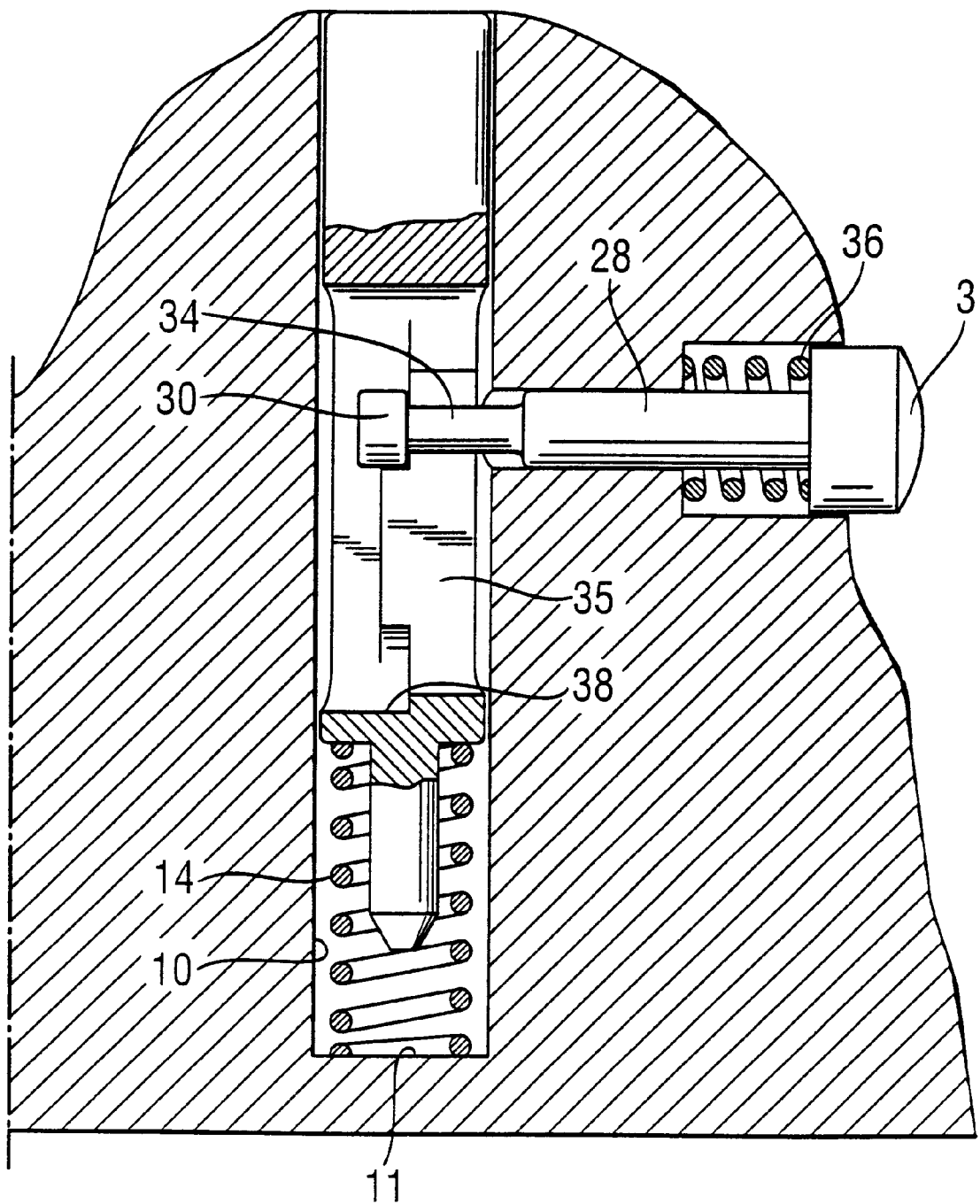
FIG. 10 shows a section corresponding to FIG. 9, showing the anchoring part in its first locked position.
Figure 11:
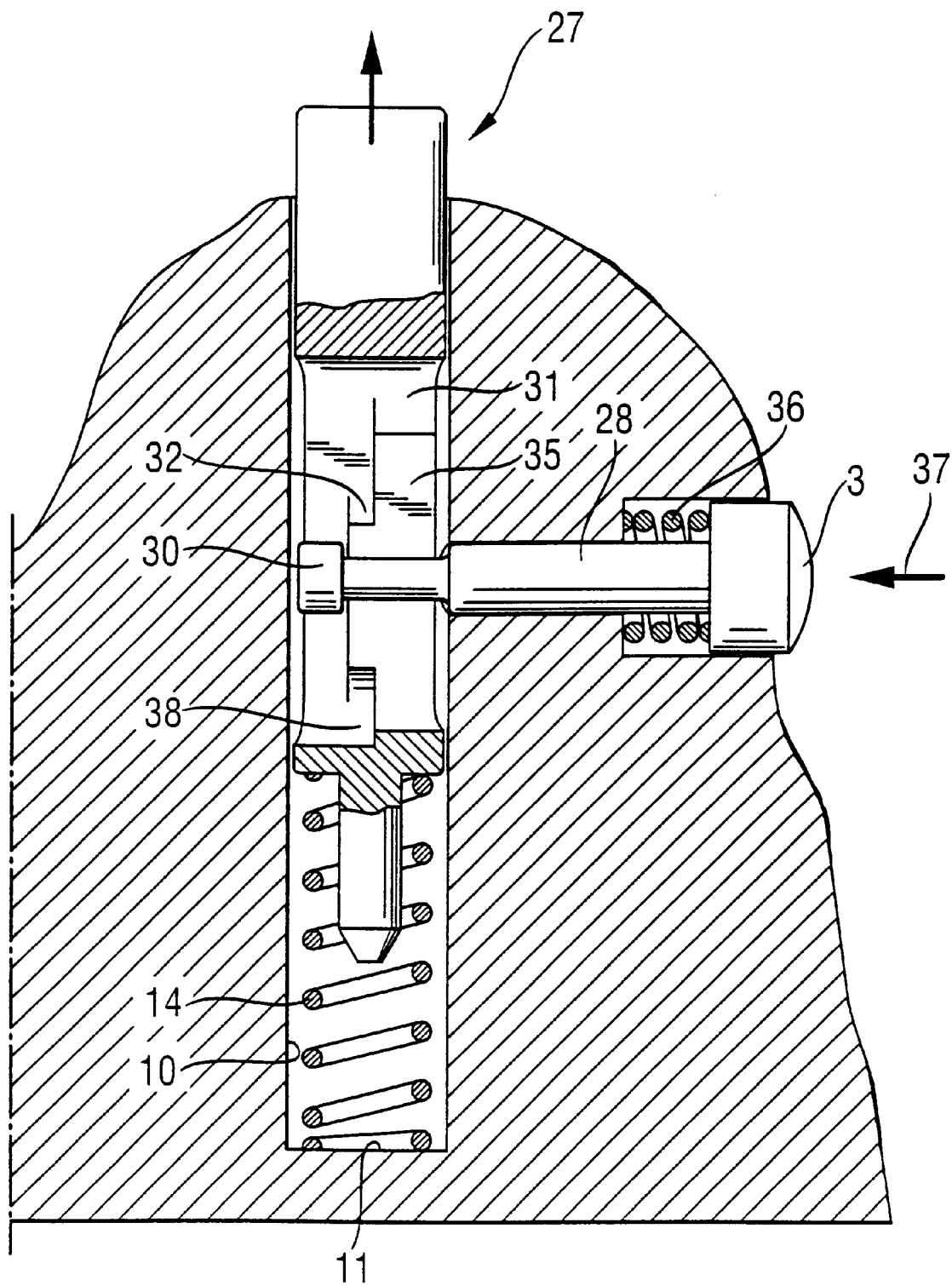
FIG. 11 shows a section corresponding to FIG. 9, showing the anchoring part as it is being driven out from the model.
Figure 12:
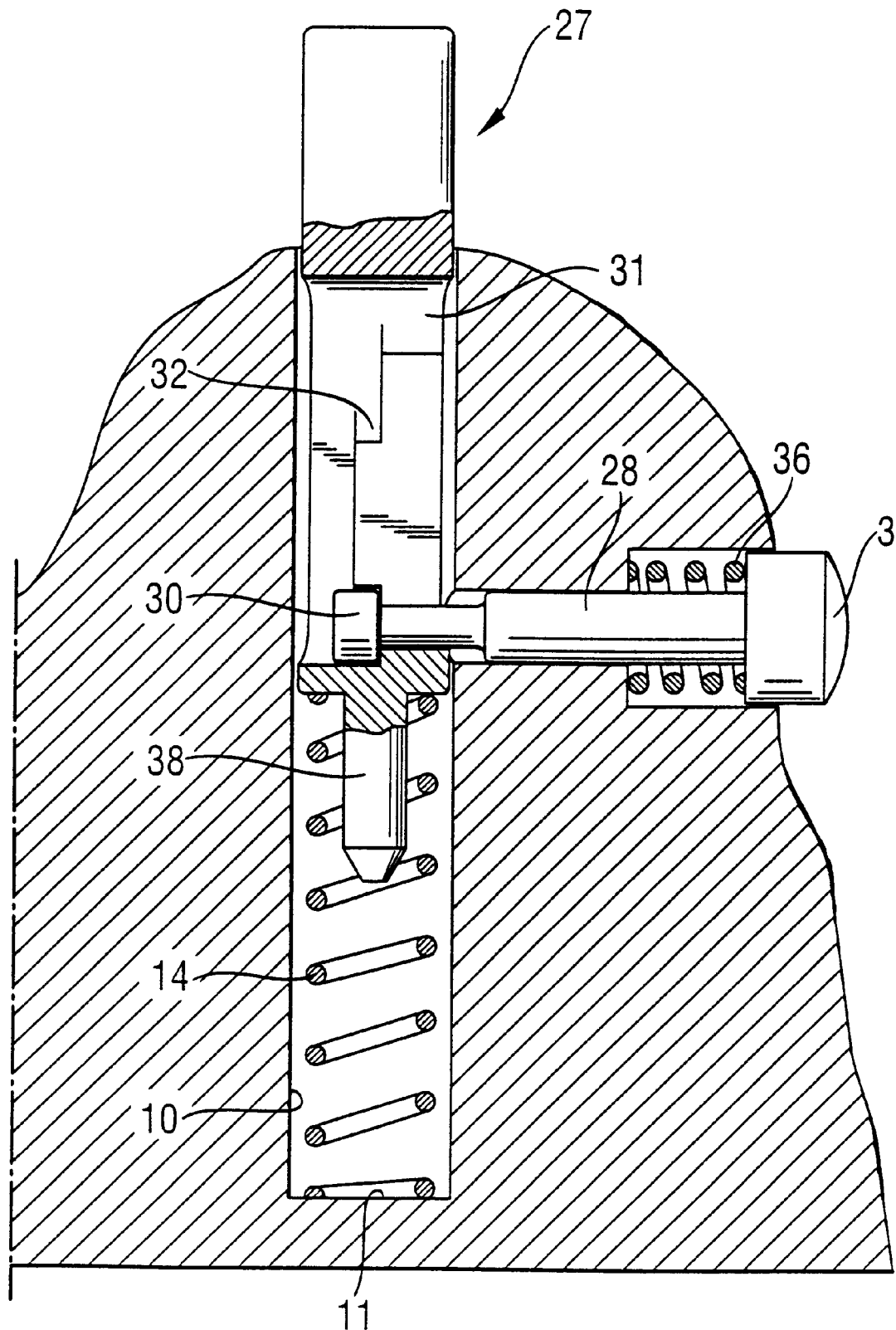
FIG. 12 shows a section corresponding to FIG. 9, showing the anchoring part in its second locked position.
Figures 13, 14:
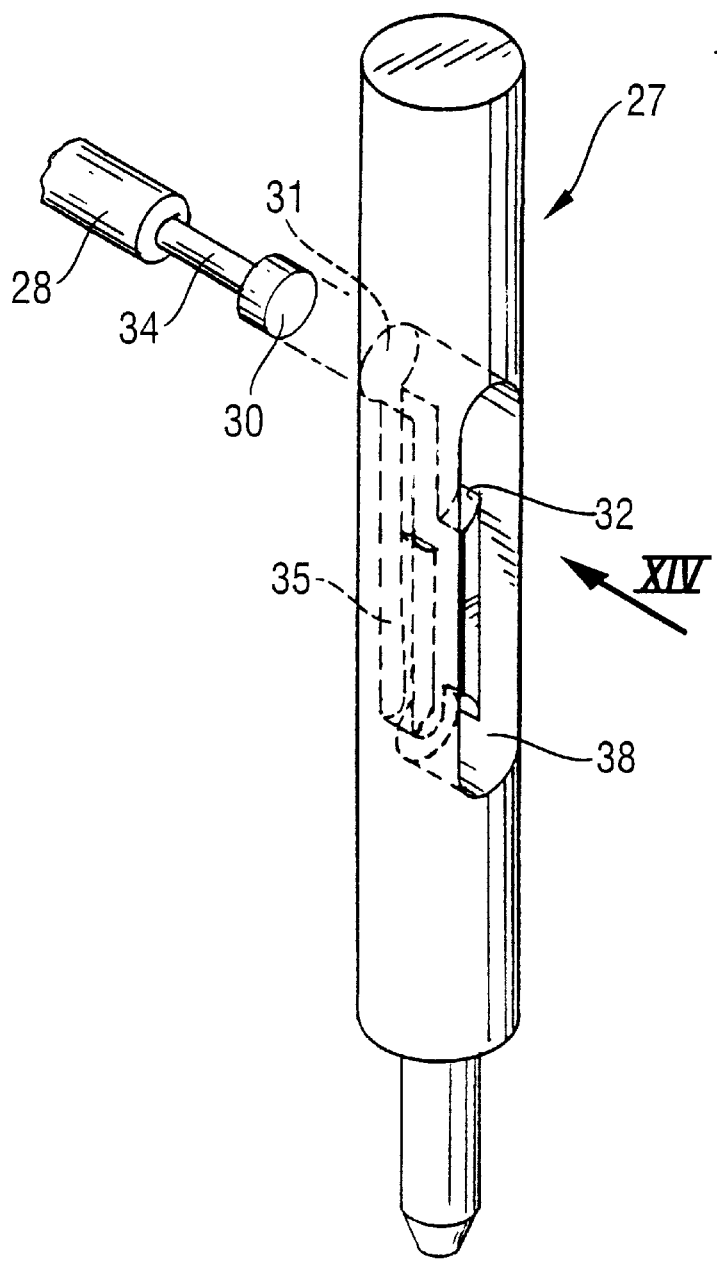
FIG. 13 shows a perspective representation of the anchoring part according to FIGS. 9 to 12.
FIG. 14 shows a partial view in the direction of the arrow XIV in FIG. 13.

In the figures, reference number 1 designates the main body of a jaw model which is provided with a multiplicity of anchoring parts 2 which, by actuation of actuating buttons 3, can be transferred from a first inward locked position (cf. FIG. 1) to a second outward locked position (cf. FIG. 2). In the first locked position, the ends of the anchoring parts 2 are flush with that surface of the main body 1 simulating a jaw arch, whereas in the second locked position they project above the surface of the main body by a certain distance in the manner of a tooth stump or the end of an implant. FIG. 3 shows a configuration for securing a bridge 4 and an individual tooth 5, while FIG. 4 shows the conditions for securing a total prosthesis 6 without plate.

Details of the structure and arrangement of the anchoring parts 2 will become evident from the other figures.

The anchoring part 2 illustrated in FIGS. 5 to 8 has a bottom part 7 and a cap 8 which is fitted on the upper end of the latter and is secured to the bottom part 7 by means of a screw 9. For receiving each anchoring part 2 there is a respective bore hole 10 in the main body 1, and between the base 11 of the bore hole 10 and a flange 12 of the bottom part 7 there is a spring 14 which encloses a rod 13 and seeks to press the anchoring part 2 out of the bore hole 10. The lower end of the bottom part 7 is guided in a sleeve 15 which is held in the bore hole 10 by the cap 8 and which is provided with a guide slot 16 whose width is only slightly greater than the diameter of a section 18 of a locking pin 19 forming an annular groove 17, which locking pin 19 holds the anchoring part 2 in FIG. 5 in its first locked position, bearing against a first limit stop 20 of the anchoring part 2. By moving the locking pin 19, arranged at right angles to the longitudinal axis of the anchoring part 2, in the direction of the arrow 21, the head piece 22 of the locking pin 19 is distanced from the first limit stop 20, and the spring 14 can move the anchoring part 2 upwards in the direction of the arrow 23 (cf. FIG. 6). The displacement path of the anchoring part 2 is limited here by the height or length of a recess 24, at the bottom end of which there is a second limit stop 25 which defines the second locked position of the anchoring part 2. In this second locked position, the anchoring part 2 is held by the locking pin 19 which has moved back into its starting position in the direction of the arrow 26.

Whereas the locking pin 19 of the anchoring part 2 is designed as a tensioning pin, FIGS. 9 to 14 show an anchoring part 27 which is locked by a locking pin 28 designed as a pressure pin. The anchoring part 27 which in this case is formed in one piece is guided directly in the bore hole 10 of the main body 1, and upon assembly it is pressed by means of a mandrel 29, counter to the action of the spring 14, into a position in which the head piece 30 of the locking pin 28 can pass through a transverse bore hole 31 of the anchoring part 27. As soon as this has taken place, the spring 14 presses the anchoring part 27 into the position shown in FIG. 10 in which the head piece 30 comes to bear against a first limit stop 32. That section 34 of the anchoring part 27 provided with an annular groove 33 is then situated in the area of a guide slot 35. If the locking pin 28 is now pressed in the direction of the arrow 37 in order to overcome the force of the restoring spring 36, the anchoring part 27 moves upwards under the action of the spring 14 (cf. FIG. 11) until it reaches its locked position shown in FIG. 12, in which the head piece 30 is locked by the second limit stop 38.

What is claimed is:

1. Jaw model for demonstrating dental work, said jaw model comprising a main body defining a jaw arch, and at least one post-shaped anchoring part simulating a tooth stump; said jaw model defining a plurality of bore holes for receiving said anchoring parts therein; means for selectively locking said anchoring part in a first locked position relative to said bore hole in which a top surface of said anchoring part is flush with an outer surface of said main body, and a second locked position relative to said bore hole in which a top surface of said anchoring part extends beyond an outer surface of said main body; and means for selectively moving said anchoring part between said first and said second locked positions, said means for moving including a spring arranged to exert a resilient force on said anchoring part in a direction towards said second locked position.

2. Jaw model according to claim 1, further including a locking pin (19; 28) for releasably locking each said anchoring part (2; 27) in said first and second locked positions.

3. Jaw model according to claim 2, wherein each said anchoring part (2; 27) has two limit stops (20, 25; 32, 38), one of said limit stops corresponding to said first locked position, and the other of said limit stops corresponding to said second locked position.

4. Jaw model according to claim 2, wherein each said locking pin (19; 28) has an actuating button (3) extending beyond an outer surface of the main body (1).

5. Jaw model according to claim 2, wherein each said anchoring part (2; 27) has a longitudinal axis, and each said locking pin (19; 28) has a longitudinal axis, said anchoring part and said locking pin being arranged such that said respective longitudinal axis intersect at an angle of 90°.

6. Jaw model according to claim 3, wherein each said locking pin (19; 28) has a section (18; 34) defining an annular groove (17; 33), said locking pin being arranged relative to said anchoring part such that said section (18; 34) of said locking pin is transversely displaceable in a guide slot (16; 35).

7. Jaw model according to claim 6, wherein the locking pin (19; 28) has an end adjoining the annular groove (17; 33), said end defining a head piece (22; 30) adapted to engage the limit stops (20, 25; 32, 38).

8. Jaw model according to claim 6, wherein the guide slot (35) is defined in the anchoring part (27).

9. Jaw model according to claim 7, wherein above the guide slot (16) defined in the anchoring part (27), a transverse bore hole (31) is defined for the head piece (30) of the locking pin (28).

10. Jaw model according to claim 6, further including a sleeve (15) enclosing said anchoring part (2) over part of its length, said guide slot (16) defined in said sleeve (15).

11. Jaw model according to claim 10, wherein the anchoring part (2) consists of a bottom part (7) guided in said sleeve and of a cap (8) screwable onto said bottom part for forming an imitation tooth stump.

12. Jaw model according to claim 11, wherein the cap (8) secures the sleeve (15) in said bore hole (10).

13. Jaw model according to claim 3, wherein each said locking pin (19; 28) has an actuating button (3) extending beyond an outer surface of the main body (1).

14. Jaw model according to claim 3, wherein each said anchoring part (2; 27) has a longitudinal axis, and each said locking pin (19; 28) has a longitudinal axis; said anchoring part and said locking pin being arranged such that said respective longitudinal axis intersect at an angle of 90°.

15. Jaw model according to claim 4, wherein each said anchoring part (2; 27) has a longitudinal axis, and each said locking pin (19; 28) has a longitudinal axis; said anchoring part and said locking pin being arranged such that said respective longitudinal axis intersect at an angle of 90°.

16. Jaw model according to claim 7, wherein the guide slot (35) is defined in the anchoring part (27).

17. Jaw model according to claim 16, further including a restoring spring (36), wherein each said locking pin (28) is a pressure pin mounted in the main body (1) and is displaceable counter to the action of the restoring spring (36).

18. Jaw model according to claim 7, further including a sleeve (15) enclosing said anchoring part (2) over part of its length, said guide slot (16) defined in said sleeve (15).

* * * * *

UNITED STATES PATENT AND TRADEMARK OFFICE
CERTIFICATE OF CORRECTION

PATENT NO.    : 6,257,895 B1
DATED         : July 10, 2001
INVENTOR(S)   : Gerd Oestreich It is certified that error appears in the above-identified patent and that said Letters Patent is hereby corrected as shown below:

Column 4,
Line 19, delete "claim 7", and substitute -- claim 17 --.

Signed and Sealed this

Thirtieth Day of April, 2002

*Attest:*

JAMES E. ROGAN
*Attesting Officer*     *Director of the United States Patent and Trademark Office*